(12) United States Patent
Kuyava et al.

(10) Patent No.: US 7,681,518 B2
(45) Date of Patent: Mar. 23, 2010

(54) PARYLENE COATED COMPONENTS FOR ARTIFICIAL SPHINCTERS

(75) Inventors: Charles C. Kuyava, Eden Prairie, MN (US); John W. Westrum, Jr., Apple Valley, MN (US); Gary J. Nachreiner, Mound, MN (US); Mona J. Inman, Minnetonka, MN (US)

(73) Assignee: AMS Research Corporation, Minnetonka, MN (US)

( * ) Notice: Subject to any disclaimer, the term of this patent is extended or adjusted under 35 U.S.C. 154(b) by 1140 days.

(21) Appl. No.: 11/295,845

(22) Filed: Dec. 7, 2005

(65) Prior Publication Data

US 2006/0083848 A1    Apr. 20, 2006

Related U.S. Application Data

(60) Division of application No. 10/211,967, filed on Aug. 2, 2002, now Pat. No. 7,011,622, and a continuation-in-part of application No. 09/526,051, filed on Mar. 15, 2000, now Pat. No. 6,558,315.

(60) Provisional application No. 60/310,005, filed on Aug. 3, 2001.

(51) Int. Cl.
*C23C 14/00* (2006.01)
(52) U.S. Cl. .......................... 118/50; 424/423
(58) Field of Classification Search ................ None
See application file for complete search history.

*Primary Examiner*—Robert A Wax
*Assistant Examiner*—Jeffrey T Palenik
(74) *Attorney, Agent, or Firm*—Jose' W. Jimenez; Kimberly K. Baxter; Gregory L. Koeller

(57) ABSTRACT

A method of depositing a coating to a surface of an inflatable component by providing a vacuum chamber system having an inner chamber positioned within an outer chamber. At least one coating material is introduced into at least one of the inner and outer chambers to deposit a coating onto an exposed surface of the component. This invention also provides methods of masking portions of surfaces of an inflatable component to prevent a coating from being deposited on the masked portion.

7 Claims, 9 Drawing Sheets

PARYLENE COATED COMPONENTS FOR ARTIFICIAL SPHINCTERS

RELATED APPLICATIONS

This application is a divisional application, under 37 C.F.R. §1.53(b), of prior application Ser. No. 10/211,967, filed Aug. 2, 2002 now U.S. Pat. No. 7,011,622 for: Parylene Coated Components for Artificial Sphincters, which claims priority to U.S. Provisional Patent Application No. 60/310,005, filed Aug. 3, 2001, for: Parylene Coated Components for Artificial Sphincters, and which is a continuation-in-part application of application Ser. No. 09/526,051, filed Mar. 15, 2000 for: Parylene Coated Components for Inflatable Penile Prosthesis, now U.S. Pat. No. 6,558,315 The entire disclosure of the prior applications are considered as being part of the disclosure of the accompanying application and are hereby incorporated by reference herein.

TECHNICAL FIELD

Incontinence is an affliction that prevents a patient from controlling waste elimination functions. As one might expect, this condition can be quite debilitating and embarrassing and may severely limit the patient's activities.

Various techniques exist for treating incontinence in patients. One such technique is surgical implantation of an artificial sphincter. One form of artificial sphincter includes an appropriately sized inflatable cuff that is positioned around either the urethra or the rectum, depending upon the nature of the incontinence. A control pump is fluidly coupled to the cuff and to a pressure-regulating balloon, both of which are positioned within the body of the patient. Under normal conditions, the cuff is inflated which causes a compression of the urethra or the rectum, thus preventing unintentional discharge. When so desired, the patient manually actuates the control pump. Fluid is then withdrawn from the cuff and forced into the pressure-regulating balloon. As this occurs, the cuff relaxes allowing the urethra or rectum to expand and open. At this point, normal waste elimination functions are permitted. The pressure-regulating balloon contains a volume of fluid that is maintained at a relatively high pressure. The control pump is provided with a fluid resistor that allows pressurized fluid to slowly return to the cuff causing it to automatically re-inflate.

The surgical implantation of such an artificial sphincter is meant to be a long-term solution to the problem of incontinence in selected patients. Thus, the materials chosen to fabricate the artificial sphincter should be biocompatible and medically safe while permanently implanted within human tissue. Furthermore, the physical configuration of the artificial sphincter must be such that patient comfort levels are maintained while achieving satisfactory compression of the urethra or rectum. Finally, the artificial sphincter should have a configuration that takes into account the surgical techniques that are required to implant the device.

With these considerations in mind, various artificial sphincters exist, having different configurations and material choices. One such artificial sphincter employs a generally rectangular inflatable member that is wrapped about the outer circumference of the urethra or the rectum, thus forming the inflatable cuff. As pressure is increased and the cuff inflates, the interior area defined by the cuff is compressed, thus achieving the desired results. The cuff may be formed from silicone, which has proven to be a reliable and medically safe material that is usually compatible with human tissue.

Due to the nature and configuration of the rectangular chamber that forms the cuff, a non-continuous, non-circular geometrical configuration is produced. That is, the wall of the cuff which forms the interior circumference, (i.e., that which is in contact with the urethra), has a series of fold lines that develop. At the position denoted by these fold lines, the silicone material forming the cuff is caused to come into contact with itself. Through the normal movement of the patient, the cuff may be caused to bend and flex, thus causing these contacting portions to move across one another. This movement is most prevalent at the corners formed by these fold lines. Generally, the fold lines will occur in the same position, and over time, the repeated movement of one portion of silicone over another may possibly lead to wear, abrasion and fatigue.

SUMMARY OF THE INVENTION

This invention provides an artificial sphincter including at least one component adapted for inflation and deflation. At least one contacting surface of the component is coated with a polymeric material adapted to expand and return to an original configuration to prevent or inhibit wear or abrasion of the contacting surface. In one embodiment, component is a cuff adapted to surround a urethra or a rectum. In another embodiment, the polymeric material is parylene and the component is made of silicon.

This invention also includes an artificial sphincter including an inflatable cuff, a control pump fluidly coupled to the inflatable cuff, and a pressure-regulating balloon fluidly coupled to the control pump. At least a portion of the artificial sphincter includes a polymeric coating adapted to expand and return to an original configuration, to reduce the coefficient of friction of a surface, and to prevent or inhibit wear or abrasion of the surface. The polymeric coating may be parylene, for example.

This invention also includes an artificial sphincter component adapted for inflation and deflation, and coated on at least one contacting surface with a polymeric material, the polymeric coating adapted to expand and return to an original configuration and to prevent or inhibit wear or abrasion of the contacting surface. In one embodiment, the artificial sphincter component is an inflatable silicon cuff adapted to surround a urethra or a rectum and the polymeric material is parylene.

This invention also provides a method for increasing the wear-resistance of a component for a flexible artificial sphincter. The wear-resistance is increased by coating a region of the component with a polymeric material adapted to expand and return to an original configuration and prevent or inhibit wear or abrasion of a contacting surface. In one embodiment, the coating step comprises a vapor deposition of a polymeric material including parylene.

Also provided by the present invention is a method for depositing a coating on a surface of an inflatable component. The method includes providing a vacuum chamber system having an inner chamber positioned within an outer chamber. The inner and outer chambers are in fluid communication through at least one conduit. An inflatable component is positioned within the inner chamber. The component is sealably attached to the conduit, so that the inner and outer chambers are no longer in fluid communication. A vacuum device is activated to apply a vacuum to at least one of the inner and outer chambers. At least one coating material is introduced into at least one of the inner and outer chambers to deposit a coating onto an exposed surface of the component.

DETAILED DESCRIPTION OF THE INVENTION

Various techniques exist for treating incontinence in patients. One such technique is surgical implantation of an artificial sphincter. An artificial sphincter generally includes a component that is adapted for inflation and deflation. This component may be an appropriately sized inflatable cuff that is positioned around either the urethra or the rectum, depending upon the nature of the incontinence. Generally the artificial sphincter includes other components, such as a control pump fluidly coupled to the cuff by a first tube, and a pressure-regulating balloon fluidly coupled to the control pump by a second tube, all of which are positioned within the body of the patient.

In a first embodiment, this invention provides an artificial sphincter including at least one component adapted for inflation and deflation. At least one contacting surface of the component is coated with a polymeric material adapted to expand and return to an original configuration to prevent or inhibit wear or abrasion of the contacting surface.

As used herein, the phrase "contacting surface" means a portion of a surface that repeatedly comes into contact with another surface in such a manner that the two surfaces move across one another. A contacting surface, for example, is often found near fold lines of an inflatable cuff, where the material forming the cuff is caused to come into contact with itself. Through the normal movement of a patient, an implanted cuff may be caused to bend and flex, causing these contacting portions to move across one another.

Figure 1:
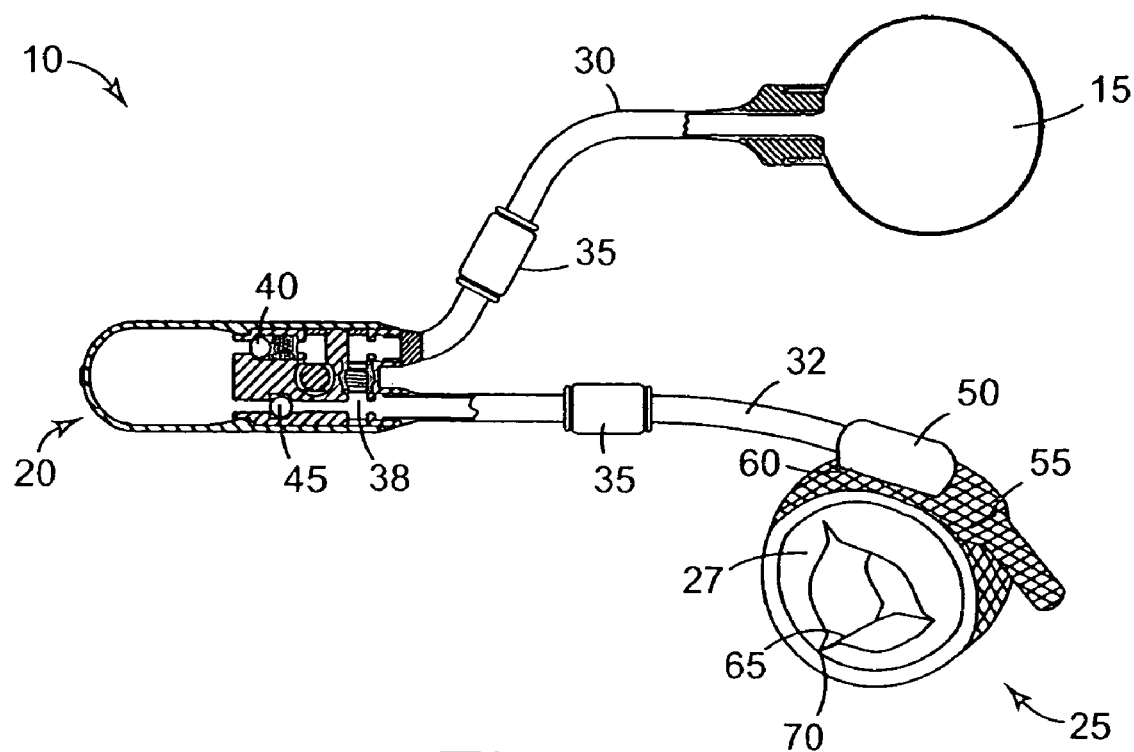
FIG. 1 is a partial sectional view of an artificial sphincter in accordance with the present invention.

An artificial urinary sphincter is illustrated in FIG. 1 and generally referred to as 10. Though a urinary sphincter is illustrated, it is to be understood that the present invention is equally applicable to an artificial bowel sphincter. One embodiment of the invention includes as a component a generally rectangular inflatable member that is wrapped about the outer circumference of the urethra or the rectum, forming an inflatable cuff. The cuff may be coated on at least one contacting surface with the polymeric material. Alternatively, any of the other components described herein may have a contacting surface coated with the polymeric material.

Artificial urinary sphincter ("AUS") 10 includes a pressure-regulating balloon 15 that is fluidly coupled to a control pump 20 via reinforced tube 30. Also fluidly coupled to control pump 20 via a second reinforced tube 32 is cuff 25. The various reinforced tubes 30, 32 are separable at connectors 35 to facilitate the implantation during a surgical procedure. Pressure-regulating balloon 15 contains a volume of fluid sufficient to cause an expansion of pressure-regulating balloon 15. As illustrated, pressure-regulating balloon 15 is in fluid communication with cuff 25 through a fluid resistor 38. This allows pressurized fluid from pressure-regulating balloon 15 to travel through fluid resistor 38 and inflate cuff 25. Fluid resistor 38 is configured so that fluid flow from pressure-regulating balloon 15 to cuff 25 is permitted, but at a relatively slow rate.

Figure 2:
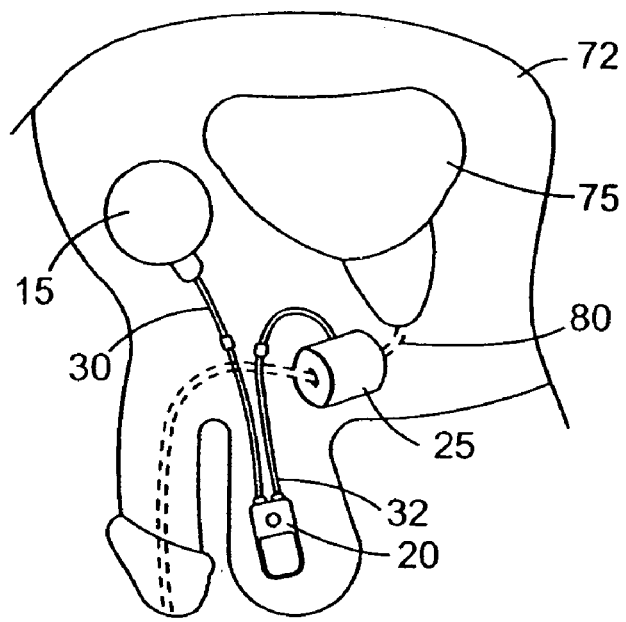
FIG. 2 is a schematic illustration of an artificial sphincter implanted within a patient.

Cuff 25 may be formed from silicone, which has proven to be a reliable and medically safe material that is usually compatible with human tissue. Cuff 25 may also be formed from other suitably flexible biocompatible materials. Cuff 25 includes a generally rectangular chamber 27. A specially constructed backing 55 is applied to one surface of chamber 27. An opening is provided in chamber 27 to which adapter 50 is adhesively bound. Adapter 50 provides an interconnection to reinforced tube 32. During implantation, reinforced tube 32 is disconnected from connector 35. Cuff 25 is positioned around the urethra 80 within the patient's abdomen 72 as illustrated in FIG. 2. As cuff 25 is wrapped around the urethra 80, adapter 50 and a portion of reinforced tube 32 are passed through a backing slit 60 within backing 55. It is this configuration that holds cuff 25 in position. Reinforced tube 32 is then coupled via connector 35 to control pump 20. The backing 55 is configured so that upon inflation of cuff 25, expansion occurs inwardly. As pressure is increased and cuff 25 inflates, the interior area defined by cuff 25 is compressed, thus achieving the desired results.

Pressure-regulating balloon 15 contains a volume of fluid that is maintained at a relatively high pressure. Under normal conditions, cuff 25 is inflated with fluid which causes a compression of urethra 80, thus preventing fluid flow from bladder 75 and effectively preventing incontinence. When the patient desires to void bladder 75, the patient manually actuates control pump 20. Upon the compression of control pump 20, the fluid contained within control pump 20 causes an outflow check valve 40 to open and forces fluid into pressure-regulating balloon 15 thus causing the internal pressure to increase. Once control pump 20 is released, outflow check valve 40 will close and an inflow check valve 45 will open (due to the generated vacuum) thus drawing fluid from inflated cuff 25 into control pump 20. As this action is repeatedly performed, cuff 25 deflates. As this occurs, cuff 25 relaxes, allowing urethra 80 to expand and open. At this point, normal waste elimination functions are permitted. Control pump 20 is provided with a fluid resistor 38. Over time, fluid from pressure-regulating balloon 15 will seep through fluid resistor 38 and automatically re-inflate cuff 25.

Referring again to FIG. 1, cuff 25 is shown as being generally deflated. As shown, chamber 27 forms the interior of cuff 25. Despite being wrapped in a generally circular configuration, the interior exposed surface formed by chamber 27 is generally not circular in nature, but rather forms a non-continuous, non-circular geometrical configuration. That is, the wall of cuff 25 which forms the interior circumference, (i.e., that which is in contact with the urethra), has a series of fold lines 65 that develop. At each termination of fold line 65 exists a fold corner 70. At the position denoted by fold lines 65, the material forming cuff 25 is caused to come into contact with itself. This contact occurs on two contacting surfaces. One contacting surface is on the interior circumference of the outside of the inflatable cuff 25, which is contact with the urethra 80. The other contacting surface is on the interior circumference of the inside of the inflatable cuff 25.

Figure 3:
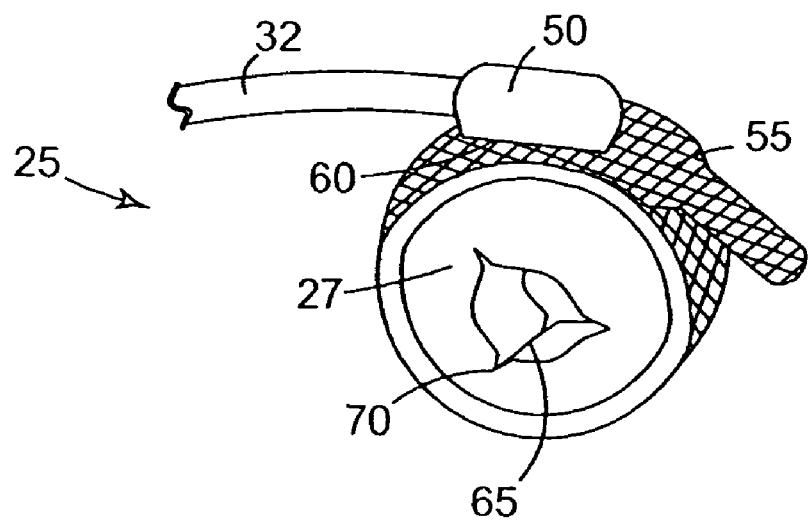
FIG. 3 is an enlarged view of a portion of the artificial sphincter of FIG. 1.

Through the normal movement of the patient, cuff 25 may be caused to bend and flex, thus causing these contacting surfaces to move across one another at and along fold line 65. This movement is most pronounced at fold corners 70. Furthermore, it is the most pronounced on an interior portion of chamber 27 at fold corner 70. The configuration of fold corner 70 along fold line 65 is also illustrated in FIG. 3. Generally, fold lines 65 will occur in the same position, and over time, the repeated movement of one portion of cuff 25 over another may possibly lead to wear, abrasion and fatigue.

In one embodiment of the artificial sphincter of the present invention, the component adapted for inflation and deflation is coated on at least one contacting surface with a polymeric material adapted to expand and return to an original configuration to inhibit wear or abrasion of the contacting surface. The artificial sphincter may have components formed from silicone or similarly flexible material that are coated with a material that increases the strength of the component while also reducing its coefficient of friction. When corners are formed along the fold lines, for example, increased wear tolerances are exhibited by allowing coated components, e.g. the cuff, to smoothly move against one another. The coating material allows one portion of the surface to slide smoothly against another portion of the surface. Thus, wear due to abrasion is significantly diminished. Furthermore, the coating material minimizes fatigue and resists contact stresses.

The efficacy of the polymeric coating for inhibiting wear or abrasion can be evaluated using conventional methods. By way of example, wear-resistance may be evaluated using a performance test known as "fold/twist cycling." The fold/twist cycling test may be done by folding the flexible component at a center point, and then rotating one end of the component about a pivot point that results at the fold. The rotated end is then rotated to a side away from the pivot point to a predetermined angle, and then back towards the pivot point to a predetermined angle, to complete a cycle. The cycling is repeated until the component fails. In the fold/twist cycling test, a leak developing in the component constitutes a failure. A higher number of successful cycles without leaking indicates a higher resistance to wear.

Figure 4:
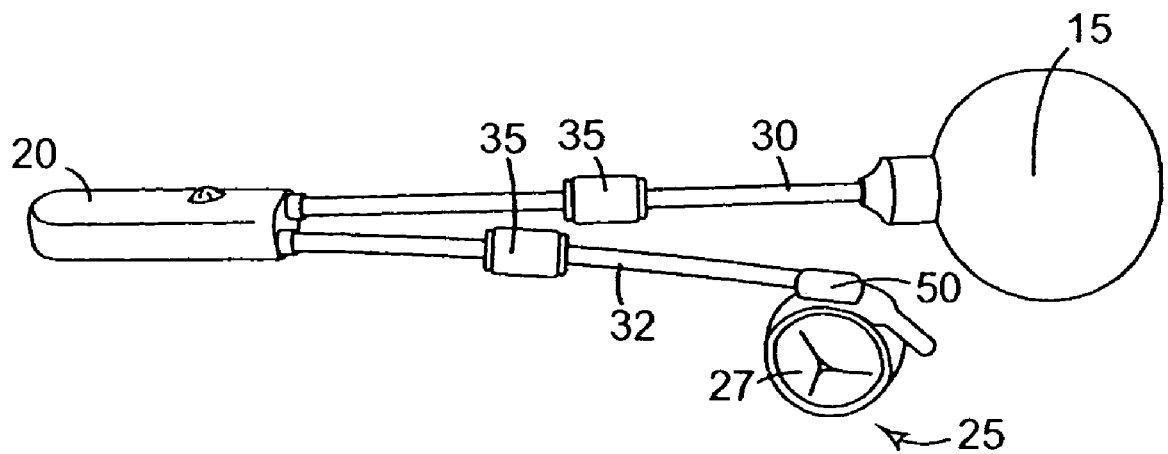
FIG. 4 is a perspective view of an artificial sphincter.

FIG. 4 illustrates AUS 10 when cuff 25 is in an inflated configuration. While the exposed or exterior portions of chamber 27 are in contact with one another along fold line 65, most of the potential concern arises from movement of fold corners 70, especially on the interior portion of chamber 27. To alleviate even the potential for such problems, it is desirable to coat one or both surfaces of chamber 27 with a layer of polymeric material. The techniques described hereinafter are to coat the interior portion of chamber 27, however, it is to be understood that the techniques are equally applicable to coating the exterior portion of chamber 27. However, if backing 55 is suitably applied to chamber 27 via an adhesive, a parylene coating should not be applied in those areas where adhesive will bind backing 55 to chamber 27.

Parylene is an ideal material for this purpose in that it provides a strong and wear-resistant surface, it is relatively slippery, it is fatigue-resistant and it allows for repeated expansion and contraction with no negative effects. Parylene is a unique material forming a high molecular weight linear crystalline polymer coating having an all-carbon backbone. During the vapor deposition process, parylene never enters the liquid state and thus an even, continuous coating occurs. Parylene has excellent dry film lubricant characteristics as indicated by its coefficient of friction, which approaches that of polytetrafluoroethylene-. Parylene will have a coefficient of friction approximately one-tenth ($\frac{1}{10}$) that of silicone when the parylene exists in a two-micrometer layer. Parylene is superior in its ability to resist wear and abrasion. Although various parylene variations are available, and each is applicable herein, parylene N is suitable in particular.

Because parylene has this low coefficient of friction, the movement that occurs over fold line 65 and especially at fold corner 70 is accommodated for a cuff such as cuff 25 having a parylene coating on at least one contacting surface. The result is that abrasion and wear is dramatically decreased due to the nature of parylene, as demonstrated by fold/twist cycling tests.

Optionally, parylene may be deposited onto only the interior surface of a cuff such as cuff 25 or onto only the exterior of a cuff such as cuff 25. In other embodiments, both the interior and exterior of a cuff 25 are coated with a thin layer of parylene. In addition, other components of the artificial sphincter may likewise be coated with parylene, such as the control pump 20, the reinforced tubes 30, 32 fluidly coupling the various components, or pressure-regulating balloon 15, for example.

When inflated, the surface of cuff 25 is caused to become taut. As such, the layers of parylene on or within cuff 25 must be able to expand somewhat. Parylene is ideal in this situation in that it will expand without breaking and once cuff 25 is deflated, will return to its original configuration. In actuality, tiny structures appear in the parylene that resemble cracks in the coating. These are not actually cracks, but areas of local yielding and this characteristic allows the coating to be very effective. While parylene is ideally suited for this application, a wide variety of other materials could be used equally well. Such alternate materials need to produce a relatively smooth coating having a sufficiently high degree of dry film lubricity, which will not bind when it is caused to contact other portions of the cuff and is able to be repeatedly expanded and then returned to its original configuration. The material should be relatively strong, to withstand the repeated contact, and have good wear characteristics so that a long component lifetime is achieved.

Parylene or a similar polymeric material may be applied during a vapor deposition process. The components to be coated are placed in a vacuum chamber to which vaporized parylene is introduced. A consistent layer of parylene then coats the items in the chamber. Generally, individual components of the artificial sphincter are coated during various stages of the manufacturing process. Thus, an important consideration is to prevent parylene from coating those areas that will eventually be bonded an adhesive to other components. While parylene has many desirable characteristics, it does not form a good surface to which to apply an adhesive. For this reason, those areas that will eventually have adhesive applied to them should be masked, or otherwise prevented from having parylene deposited thereon.

The techniques used to control the application of parylene to the cuff will depend on which areas of the cuff are to have parylene applied thereto. One technique of the present invention for applying parylene is to perform the deposition technique prior to the application of a backing material. An opening (for receiving a connective adapter) in the cuff is covered with an adhesive bearing member while the cuff is in a deflated and compressed state. The cuff is then placed in a deposition chamber and parylene is deposited. If it is desired to coat the opposite surface of the cuff, the cuff is reversed and the adhesive mask is placed on an opposite side of the opening and the process is repeated.

Figure 5:
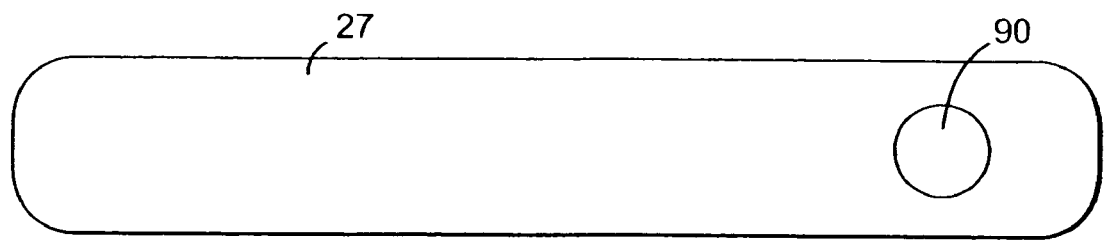
FIG. 5 is an illustration of an inflatable cuff prior to manufacture.
Figure 6:
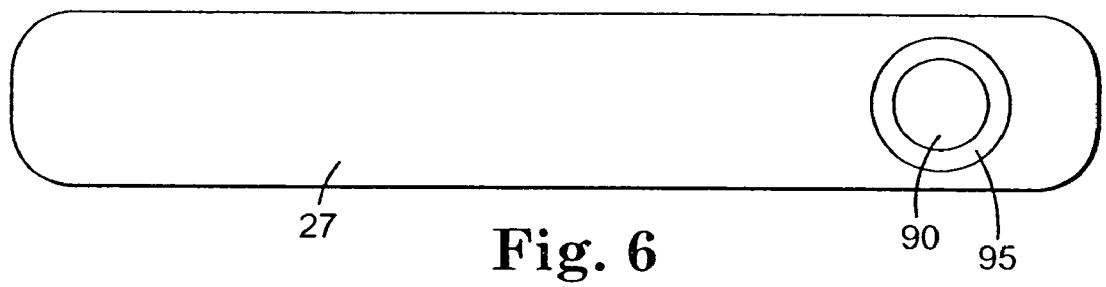
FIG. 6 is an illustration of the inflatable cuff of FIG. 5 with a mask in place in accordance with the present invention.
Figure 7:
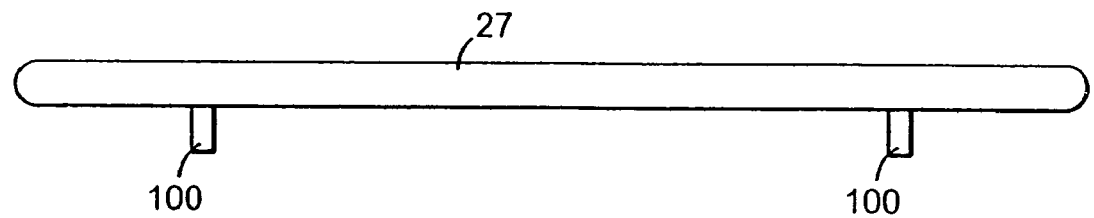
FIG. 7 is a side view of the cuff of FIGS. 5 and 6 illustrating one method of support within a vapor deposition chamber in accordance with the present invention.
Figure 10:
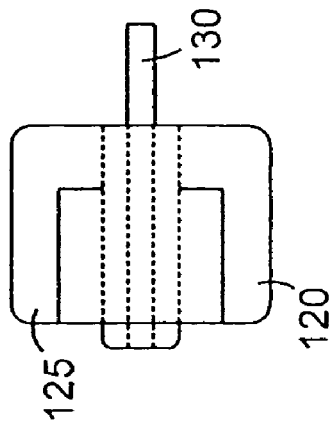
FIG. 10 is side view of the LUER-barbed fitting in accordance with the present invention.

FIG. 5 illustrates a top planar view of a chamber 27 as it exists prior to having backing 55 and adapter 50 attached thereto. Assuming an interior portion of chamber 27 is to be vapor coated, chamber 27 is reversed thus exposing its interior portion. Adapter hole 90 is provided so that adapter 50 may be attached thereto via an appropriate adhesive. Because an adhesive is to be used, the area immediately surrounding adapter hole 90 should not be coated with parylene. One technique to accomplish this is to apply a masking material 95 over adapter hole 90 utilizing an appropriate adhesive (FIG. 6). Once so prepared, chamber 27 is ready for the vapor deposition process chamber 27 with its interior portion exposed, is flattened and either supported over a grate or a number of supports 100 that are positioned in areas not likely to incur fold lines (FIG. 7). This allows the parylene coating process to cover a majority of the surface area. If it is desired to coat the exterior surface of chamber 27, the process is simply performed with the exterior portion of chamber 27 exposed and the appropriate masking material 95 disposed over adapter hole 90. While various materials can be used to form masking material 95, some examples including placing a plastic member over the desired area and relying on an adhesive to hold it in place. The adhesive could be applied separately or already be an integral part of plastic member.

In another embodiment of the present invention, a component adapted for inflation and deflation, preferably the inflatable cuff, includes an opening. Masking a portion of the component is accomplished by (i) inserting a cap through the opening so that a portion of the cap is in contact with a peripheral region of the component surrounding the opening, (ii) securing a member to the cap so that a portion of the component including the peripheral region is sandwiched between the cap and the member such that the polymeric material does not coat the portion sandwiched between the cap and the member. In other embodiments, a vent tube is placed through the cap such that fluid may selectively be permitted to flow through the tube. In another embodiment, securing a member to the cap includes placing a washer between the cap and member so that the portion of the component including the peripheral region is sandwiched between the cap and the washer.

Figure 12:
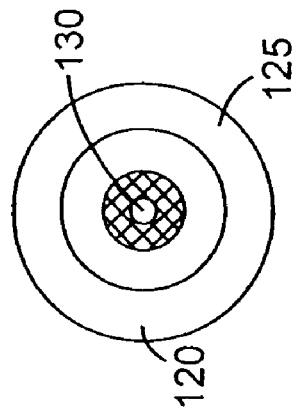
FIG. 12 is an end view of the LUER-barbed fitting of FIG. 10 in accordance with the present invention.
Figure 9:
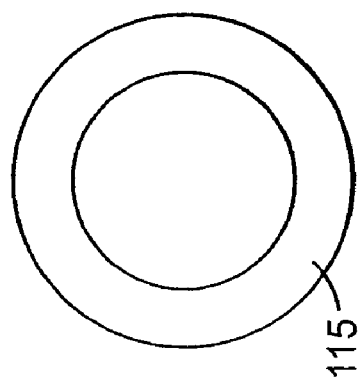
FIG. 9 is a top planar view of a washer in accordance with the present invention.
Figure 8:
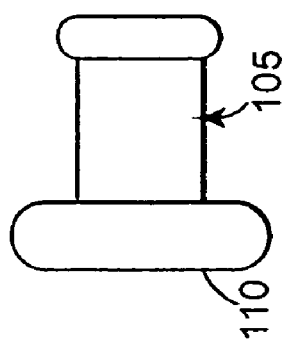
FIG. 8 is a side view of a LUER cap in accordance with the present invention.
Figure 11:
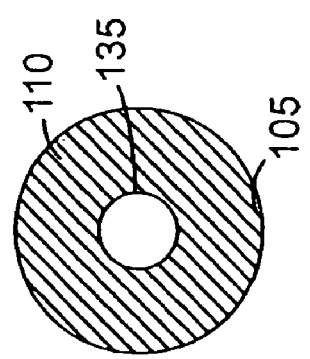
FIG. 11 is an end view of the LUER cap of FIG. 8 in accordance with the present invention.

As an alternative to using masking material 95, the present invention also provides for a masking system 140 as illustrated in FIGS. 8 through 13. The masking system 140 includes: a LUER cap 105 having an interior surface 110; a washer 115 that is preferably constructed from silicone; and a LUER barbed fitting 120, having an interior side 125 and a vent tube 130 disposed therethrough. FIG. 11 illustrates the interior surface 110 of LUER cap 105 and the positioning of a vent hole 135 therethrough. FIG. 12 illustrates the interior side 125 of LUER barbed fitting 120.

Figure 13:
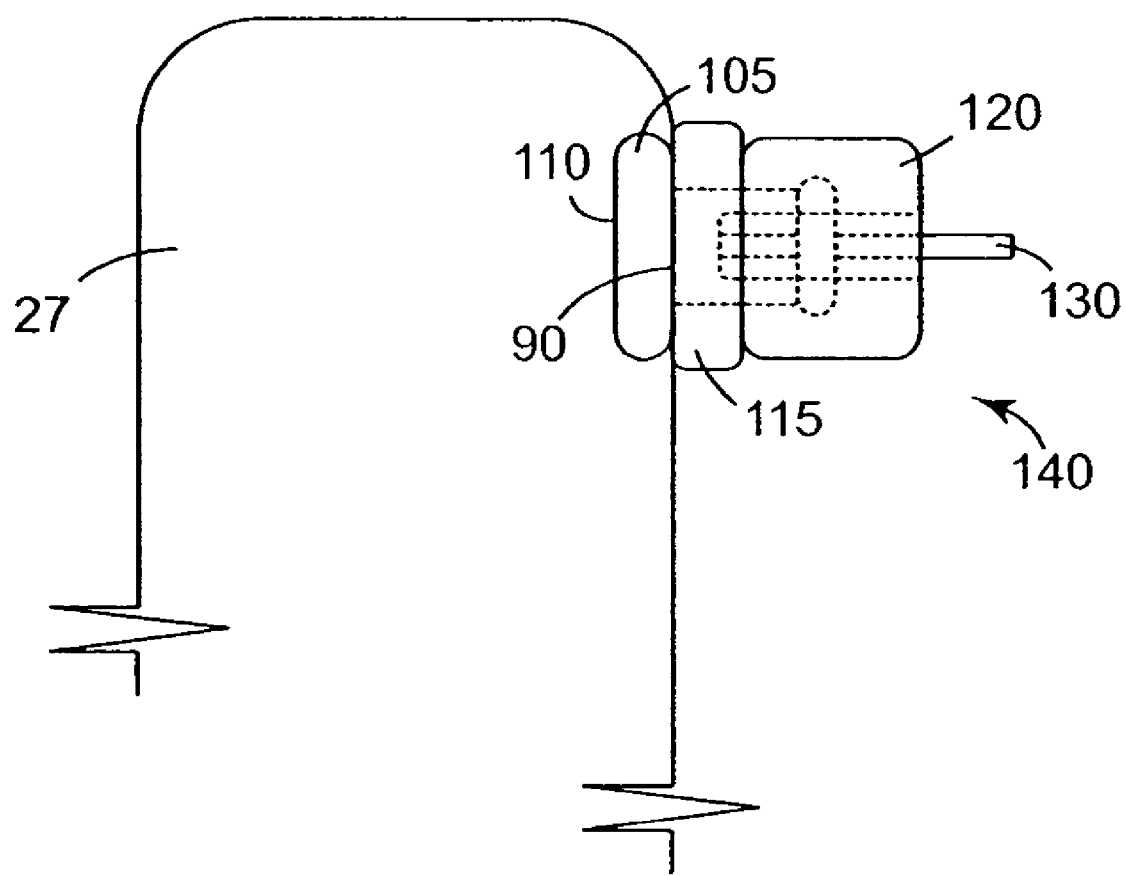
FIG. 13 is a side view of the LUER cap attached to a LUER-barbed fitting with a washer disposed therebetween in accordance with the present invention.

Referring to FIG. 13, a chamber 27 is prepared so that the surface to be coated with parylene is exposed. That is, if it is desired to coat the interior surface of chamber 27, chamber 27 must be reversed. Interior surface 110 of LUER cap 105 is placed within chamber 27 by passing it through adapter hole 90. Silicone washer 115 is placed over a portion of LUER cap 105 and contacts an area of chamber 27 immediately surrounding adapter hole 90. This area of chamber 27 is essentially sandwiched between silicone washer 115 and LUER cap 105. Subsequently, LUER barbed fitting 120 is positioned with interior side 125 abutting washer 115 and LUER barbed fitting 120 is screwed to secure washer 115 against LUER cap 105.

Due to the nature of the parylene deposition process, an even coating can be formed on interior surfaces by simply allowing vaporized parylene to pass through a relatively small channel, such as vent tube 130. Thus, if desired, both internal and external surfaces of chamber 27 can be vapor coated simultaneously by allowing vent tube 130 to remain open during the deposition process. Alternatively, vent tube 130 can be sealed so that only the exposed surfaces of chamber 27 are vapor-coated.

Vent tube 130 as thus positioned provides access to the interior of chamber 27 and allows for proper venting during placement within the vacuum chamber. LUER cap 105, washer 115 and LUER barbed fitting 120 together form a masking system 140 that can be used to occlude adapter hole 90 so as to prevent parylene (or a like material) from being deposited on an area immediately surrounding adapter hole 90 on chamber 27. Masking system 140 also serves the purpose of providing an assembly to support chamber 27 during the deposition process so that the remainder of the area of chamber 27 can be evenly and entirely coated.

Figure 14:
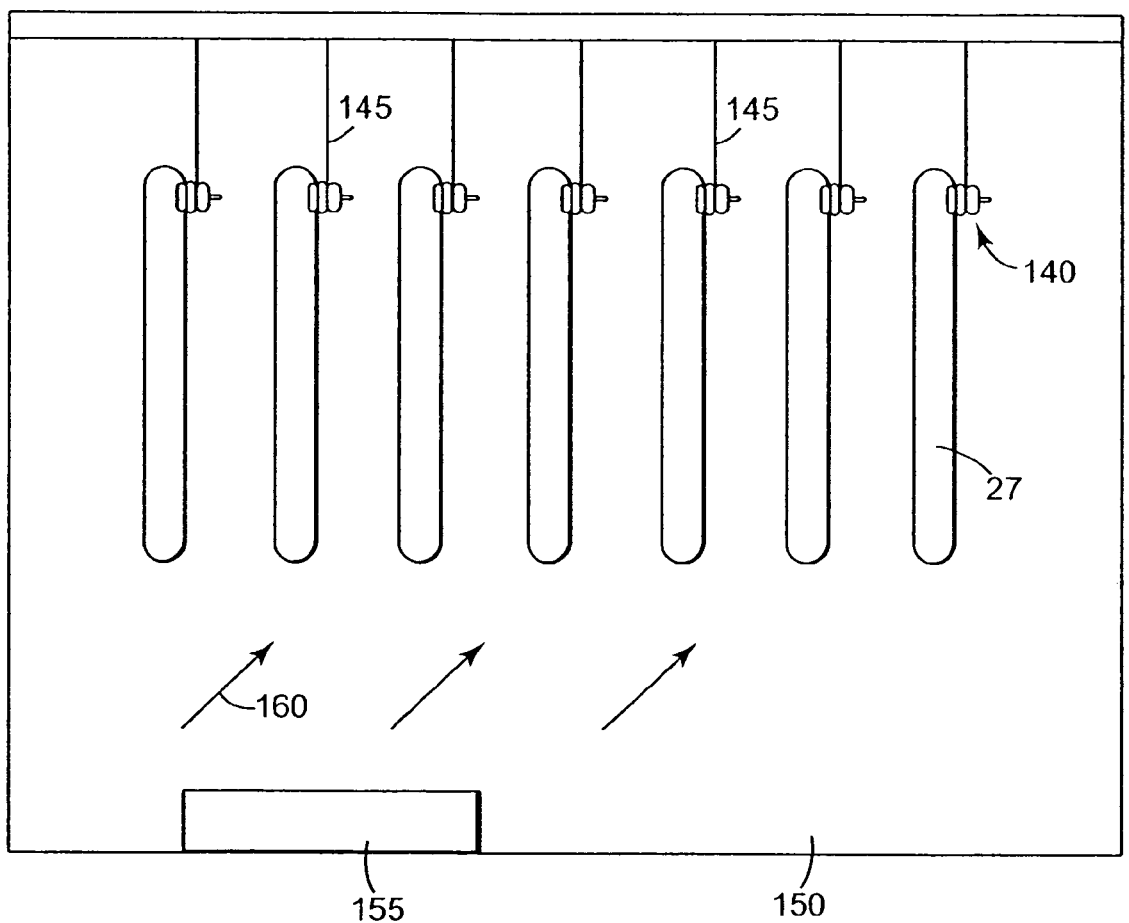
FIG. 14 is a schematic illustration of a plurality of masked cuffs suspended within a deposition chamber in accordance with the present invention.

A parylene coating may be deposited to provide the component or the artificial sphincter of the present invention using a conventional deposition chamber. FIG. 14 illustrates a deposition chamber 150 with a plurality of chambers 27 being suspended by their attached masking systems 140 from hangers 145. A vacuum is created within deposition chamber 150 by vacuum device 155. As can be appreciated, it is necessary to provide vent tubes 130 so that while a vacuum is being generated within deposition chamber 150, the interior of chambers 27 are allowed to vent so that they are not caused to burst by the reduction in surrounding pressure. Vaporized parylene 160 is then introduced into deposition chamber 150, thus achieving a uniform coating over the exposed portions of chambers 27 (and if vent tubes 130 are open, within chambers 27 as well). Parylene may be introduced, for example, by providing a container holding a condensed form of parylene, such as a liquid or solid. Parylene may alternatively be introduced directly into the chamber in vapor form.

The thickness of the parylene coating is dependent on the time the chamber 27 remains exposed to parylene vapor in deposition chamber 150. The parylene may be coated on the chamber 27 to a thickness of between 0.000040-0.000120". Ideally, the parylene should be about 0.000040-0.000080" with a layer of 0.000060" being optimal. Too thin of a layer will not yield the desired wear characteristics nor will it yield the desired coefficient of friction. Too thick of a layer may make the component too stiff and will also diminish the enhancement of wear characteristics.

Once the chambers 27 have been properly coated, they are ready for the next step of the process. This may be to reverse the chambers 27 and vapor-coat the opposite side thereof. This would only be necessary if it is desired to coat both the interior and exterior surface of chamber 27 and the size of chamber 27 is such that proper coating is not achieved merely through vent tube 130. Though not shown, it is to be understood that if the exterior portion of chamber 27 is to be coated with a layer of parylene, a portion of chamber 27 that will receive adhesive to bind backing 55 thereto should be appropriately masked prior to deposition.

Figure 15A:
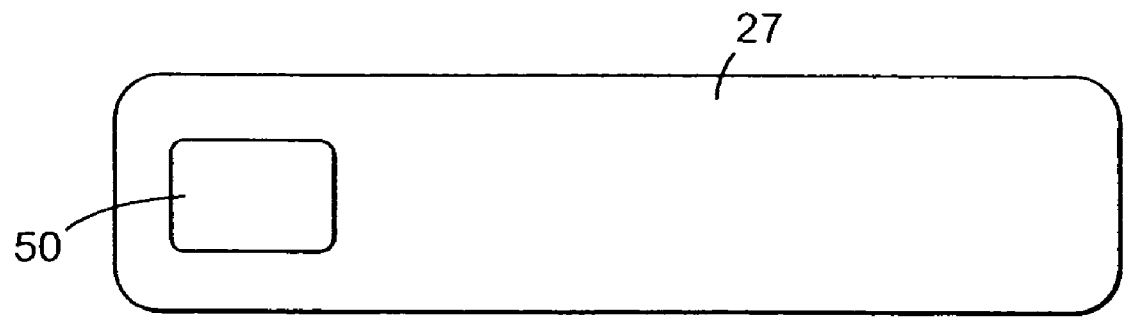
FIG. 15A is an illustration of the inflatable cuff of the present invention with an adapter attached to the adapter hole.
Figure 15B:
FIG. 15B is another illustration of the inflatable cuff of the present invention with an adapter attached to the adapter hole.

The parylene-coated chamber 27 is removed from deposition chamber 150. The masking system 140 is then removed from chamber 27. An appropriate adapter 50 is adhered to chamber 27 coaxially with adapter hole 90. Backing 55 is then applied to one side of chamber 27. This forms a completed cuff 25 that is ready to be coupled with the remainder of the artificial sphincter and implanted within a patient. In addition to the cuff, all or a portion of control pump 25 and reinforced tubes 30, 32 can be appropriately masked and coated with parylene. FIGS. 15A-B show a silicon chamber 27 having an adapter 50 sealably positioned within an adapter hole 90.

As a further alternative to using masking material 95, the present invention also provides an additional masking system 175 capable of depositing a desired quantity of parylene on the interior portion of a silicon chamber 27, without requiring the silicon chamber 27 to be reversed. In addition, the present embodiment permits the application of parylene to the interior portion of the silicon chamber 27 following attachment to a cuff 25, following the application or impregnation of the exterior surface of the silicon chamber 27 with a medicament, or both.

This embodiment provides a method of depositing a coating to a surface of an inflatable component by providing a vacuum chamber system having an inner chamber position within an outer chamber. The inner and outer chambers are in fluid communication through at least one conduit. An inflatable component is positioned within the inner chamber. The component is sealably attached to the conduit so that the inner and outer chambers are no longer in fluid communication. A vacuum device is activated to apply a vacuum to at least one of the inner and outer chambers. At least one coating material is introduced into at least one of the inner and outer chambers to deposit a coating onto an exposed surface of the component.

In one embodiment, activating a vacuum device includes activating a first vacuum device to apply a first vacuum to the outer chamber and activating a second vacuum device to apply a second vacuum to the inner chamber, wherein the second vacuum has a lower pressure than the first vacuum. In another embodiment, introducing at least coating material includes introducing a first coating material into the outer chamber to deposit a first coating onto an exposed first surface of the component, and introducing a second coating material into the inner chamber to deposit a second coating onto an exposed second surface of the component. The first coating may be parylene and the second coating may be a material selected from the group consisting of antibiotics, medicaments and therapeutic agents, for example.

Figure 16A:
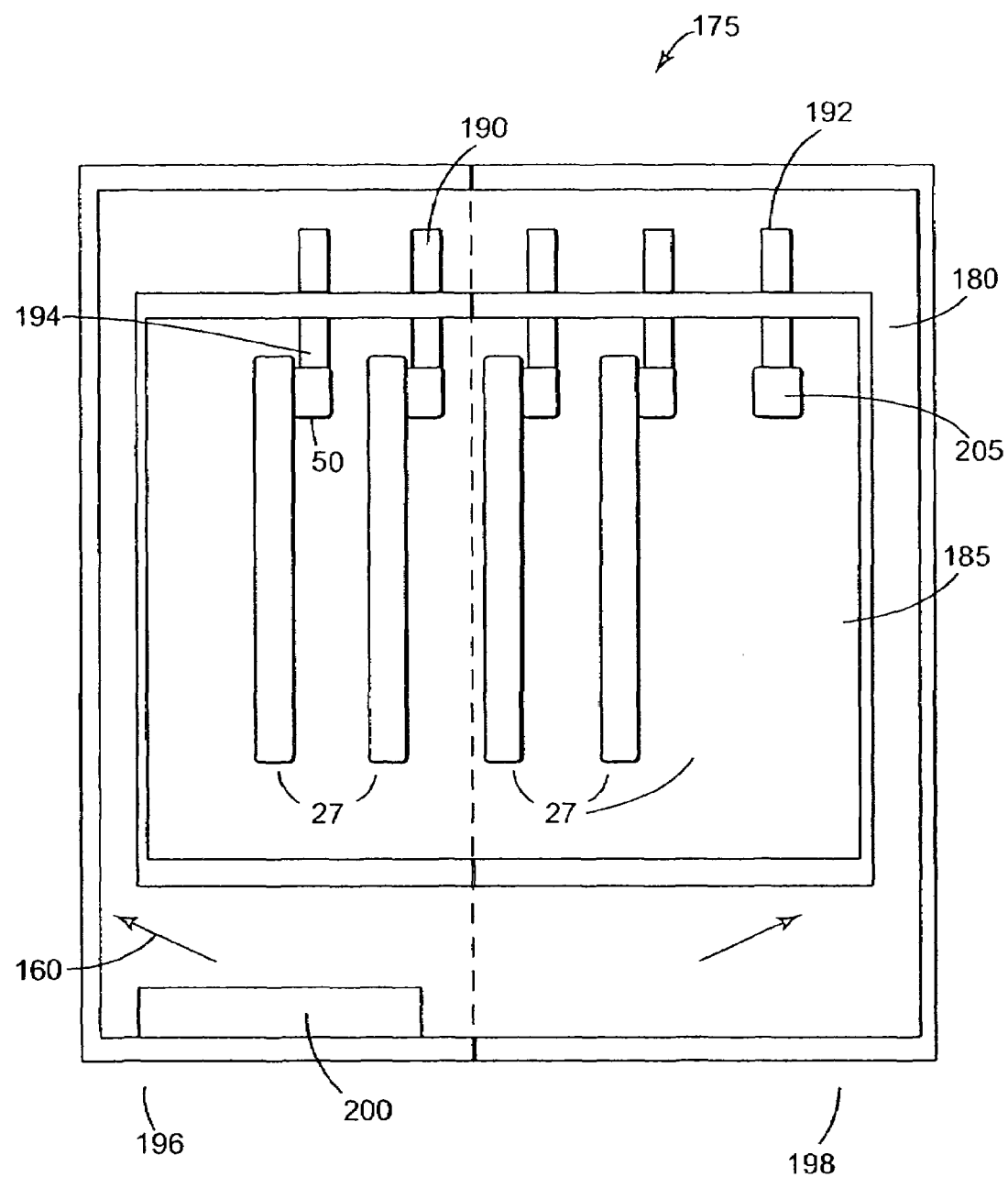
FIG. 16A is a schematic illustration of a plurality of inflatable cuffs suspended within a deposition chamber in accordance with the present invention.
Figure 16B:
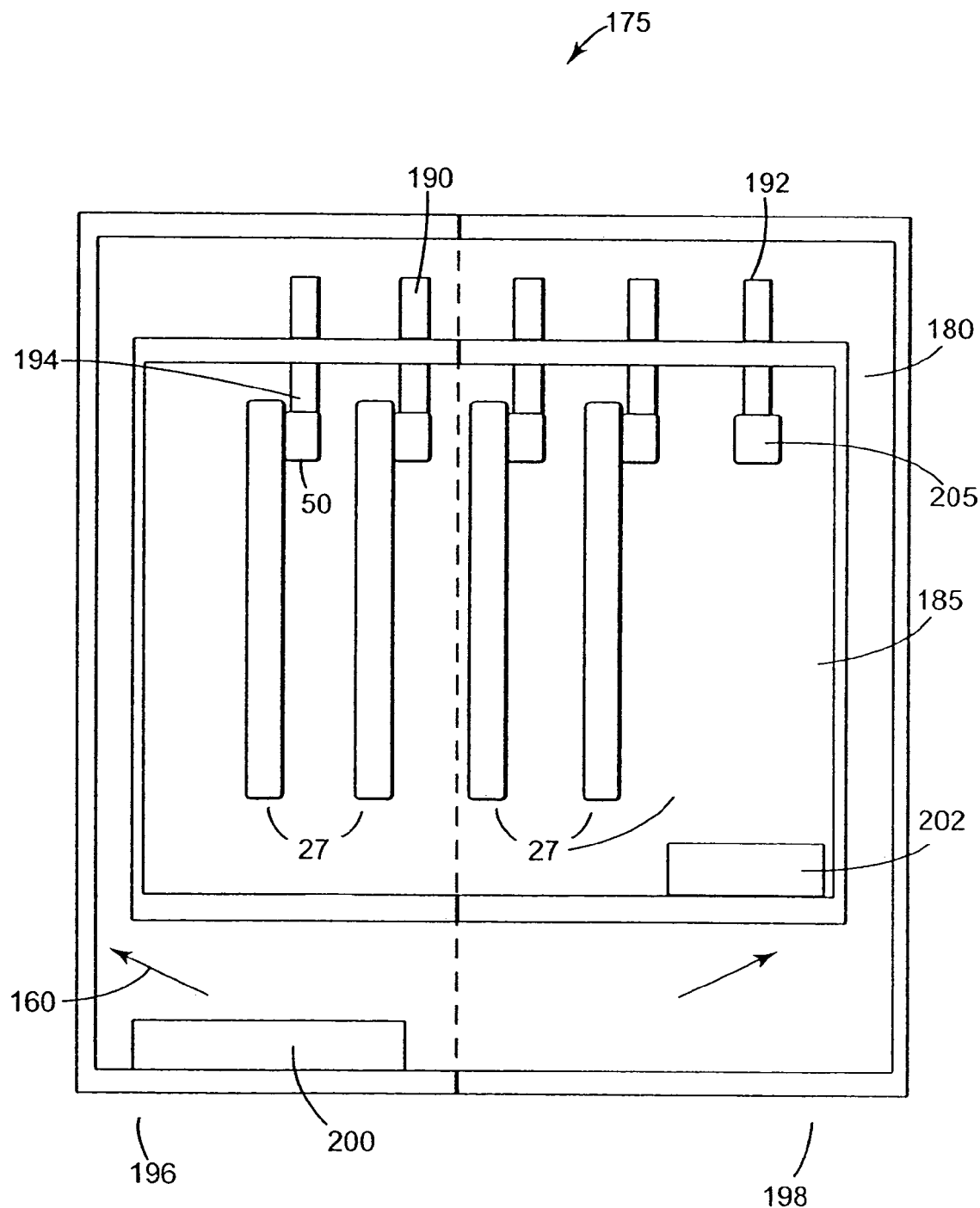
FIG. 16B is a schematic illustration of another embodiment of the present invention having a plurality of inflatable cuffs suspended within a multiple chamber deposition system.

FIGS. 16A-B illustrate a multiple chamber vapor deposition device 175. As shown in FIGS. 16A-B, the deposition chamber 175 comprises an outer chamber 180 and an inner chamber 185. The masking system 175 of the present embodiment further comprises at least one material conduit 190 having a first end 192 terminating within the outer chamber 180 and a second end 194 terminating within the inner chamber 185. Ideally, the second end 194 of the material conduit 190 is capable of sealably engaging the adapter 50 positioned on the silicon chamber 27. Those skilled in the art will appreciate the material conduit 190 may be manufactured from a variety of materials, including, for example, silicone, elastomers, various plastics, acrylics, acetates, ceramics, various metals, or other materials capable of transporting vapors with a vacuum. A shown in FIGS. 16A-B, the deposition chamber 175 of the present invention may comprise a first half 196 and a second half 198, wherein the first and second halves, 196 and 198, respectively, cooperatively form a sealed environment and isolate the inner chamber 185 from the outer chamber 180.

To apply parylene to a silicon chamber 27, the user sealably affixes an adapter 50 to the silicon chamber 27. As shown in FIGS. 16A-B, at least one silicon chamber 27 having an adapter 50 attached thereto is positioned within the inner chamber 185, such that the adapter 50 sealably engages a material conduit 190. Unused material conduits 190 are sealed using a sealing cap 205, thereby isolating the inner chamber 185 from the outer chamber 180. A vacuum is created in the outer chamber 180 and inner chamber 185. To effectuate deposition of parylene on the inner portion of the silicon chamber 27, the vacuum pressure created in the inner chamber 185 is equal to or slightly greater than the vacuum pressure applied to the outer chamber 180. As such, at least one vacuum device 200 is in communication with the outer chamber 180 and the inner chamber 185. FIG. 16B shows an alternate embodiment of the present invention having a first vacuum device 200 is in communication with the outer chamber 180 and a second vacuum device 202 is in communication with the inner chamber 185.

Vaporized parylene 160 is then introduced to the outer chamber 180. A uniform coating of parylene is deposited over the interior portion of the silicon chamber 27 which is in communication with the outer chamber 180 through the material conduit 190.

If desired, the exterior portion of the silicon chamber 27 may be coated using the present system prior to, during, or following the application of parylene. Vaporized deposition material may be introduced to the inner chamber 185 under vacuum, resulting in a uniform coating of deposition material to the exterior portion of the silicon chamber 27. Those skilled in the art will appreciate the deposition material applied to the exterior portion of the silicon chamber 27 may include, without limitation, antibiotics, medicaments, or other therapeutic materials.

The embodiments of the invention disclosed herein are illustrative of the principles of the invention. Other modifications may be employed which are within the scope of the invention. By way of example, the artificial sphincter of the present invention may be employed to surround an esophagus or other bodily canal, for example. Accordingly, the present invention is not limited to that precisely as shown and described in the present specification.

What is claimed:

1. A method of depositing a coating to a surface of an inflatable component, comprising:
    providing a vacuum chamber system having an inner chamber positioned within an outer chamber, said inner and outer chambers in fluid communication through at least one conduit;
    positioning an inflatable component within the inner chamber;
    sealably attaching the component to the conduit, whereby the inner and outer chambers are no longer in fluid communication;
    activating a vacuum device to apply a vacuum to at least one of the inner and outer chambers; and
    introducing at least one coating material into at least one of the inner and outer chambers to deposit a coating onto an exposed surface of the component.

2. The method of claim 1 wherein activating a vacuum device includes:

activating a first vacuum device to apply a first vacuum to the outer chamber; and activating a second vacuum device to apply a second vacuum to the inner chamber.

3. The method of claim 2 wherein the second vacuum is characterized by a lower pressure than the first vacuum.

4. The method of claim 1, wherein the coating comprises parylene.

5. The method of claim 1 wherein introducing at least one coating material includes:

introducing a first coating material into the outer chamber to deposit a first coating onto an exposed first surface of the component; and introducing a second coating into the inner chamber to deposit a second coating onto an exposed second surface of the component.

6. The method of claim 5 wherein the first coating comprises parylene.

7. The method of claim 5 wherein the second coating comprises a material selected from the group consisting of: antibiotics, medicaments, and therapeutic agents.

* * * * *